United States Patent [19]

Firestone

[11] 4,342,758

[45] Aug. 3, 1982

[54] ALLYLSULFOXIDE ENZYME INHIBITORS

[75] Inventor: Raymond A. Firestone, Fanwood, N.J.

[73] Assignee: Merck & Co., Inc., Rahway, N.J.

[21] Appl. No.: 147,658

[22] Filed: May 7, 1980

Related U.S. Application Data

[63] Continuation-in-part of Ser. No. 66,603, Aug. 15, 1979, abandoned.

[51] Int. Cl.$^3$ ............................................. C07D 501/36
[52] U.S. Cl. ..................................... 424/246; 544/26; 544/27; 544/28; 544/30; 544/29
[58] Field of Search .................... 424/246; 544/16, 30, 544/21, 28, 26, 27, 30, 29

[56] References Cited

U.S. PATENT DOCUMENTS

| | | | |
|---|---|---|---|
| 3,369,025 | 2/1968 | Bolhofer et al. | 260/295 |
| 3,652,646 | 3/1972 | Leigh et al. | 260/473 G |
| 3,950,542 | 4/1976 | Kalopissis | 424/316 |
| 4,049,806 | 9/1977 | Beeby | 544/16 |
| 4,112,087 | 9/1978 | Beeby | 544/16 |

FOREIGN PATENT DOCUMENTS

| | | |
|---|---|---|
| 2226406 | 11/1974 | France . |
| 2320758 | 3/1977 | France . |
| 2372630 | 6/1978 | France . |

OTHER PUBLICATIONS

Walsh, Horizons Biochem. Biophys. 3, 36–81 (1977).
Mislow et al., JACS, 90, 4869 (1968).
Mislow et al., JACS, 92, 2100 (1970).
Evans et al., JACS, 94, 3672 (1972).

*Primary Examiner*—Nicholas S. Rizzo
*Attorney, Agent, or Firm*—William H. Nicholson; Mario A. Monaco

[57] ABSTRACT

Organic sulfoxides having a latent allyl group bound to the sulfur are enzyme inhibitors of the suicide or $K_{cat}$ type.

6 Claims, No Drawings

ALLYLSULFOXIDE ENZYME INHIBITORS

BACKGROUND OF THE INVENTION

This is a continuation-in-part of copending application Ser. No. 066,603, filed Aug. 15, 1979 now abandoned.

This invention is concerned with a novel class of enzyme inhibitors of the suicide or $K_{cat}$ type in which the latent reactive group is an allylsulfoxide which is in reversible equilibrium with an allyl sulfenate:

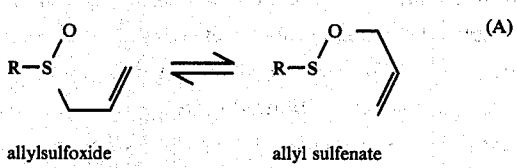

allylsulfoxide      allyl sulfenate

In particular, this invention is concerned with inhibitors of transpeptidase and $\beta$-lactamase of the allylsulfoxide-allyl sulfenate type which are useful as antibacterial agents.

Suicide enzyme inhibitors are substances bearing a latent reactive group that is unmasked by the target enzyme itself, and which after being unmasked, immediately reacts with the enzyme in an irreversible manner, inactivating it. Enzyme inhibitors of the suicide type are known in the art but until now almost invariably have employed a Micheal acceptor as the reactive species and these are described by Walsh in *Horizons Biochem. Biophys.*, 3, 36–81 (1977).

The allylsulfoxide-allyl sulfenate equilibrium of reaction scheme A) is also known in the art and has been studied as an interesting chemical reaction by Mislow et al., *J. Amer. Chem. Soc.*, 90, 4869 (1968); 92, 2100 (1970) and Evans et al., *J. Amer. Chem. Soc.*, 94, 3672 (1972). Generally, allylsulfoxides are unreactive, but allyl sulfenates are highly reactive electrophiles, and would be expected to capture almost any nucleophile (Nu) in an enzyme that happens to be near it at the moment it is formed:

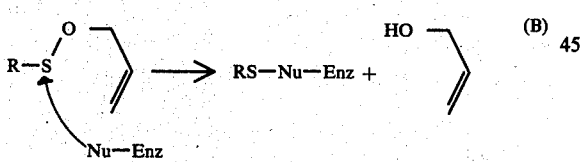

Usually the nucleophile is one from the protein portion (prosthetic group) of the enzyme, such as sulfhydryl, amino, hydroxy, imidazolyl or the like. Once the nucleophile is sulfenylated, the enzyme is altered from its native, active form and can no longer function in its intended role as a biochemical catalyst.

The allylsulfoxide-allyl sulfenate rearrangement is facilitated by the nature of the R group attached to the sulfur: the stronger the electron withdrawing nature of R the better, for exampe, p-nitrophenyl. Steric acceleration of the rearrangement is also provided by bulky o-substituted such as o-alkyl and o,o'-dialkyl when R is substituted-phenyl. Bulky groups such as alkyl and chloro substituted on the carbon chain adjacent to the sulfur atom also provide steric acceleration. Another type of electronic acceleration of the rearrangement is provided by having an electron withdrawing group, such as cyano, alkoxycarbonyl or the like substituted on the carbon $\beta$- to the sulfur atom or, in other words, on the middle carbon of the allyl group.

In the present invention, the latency of the allylsulfoxide group is secured as a $\beta$-halosulfoxide or as a vinylsulfoxide, neither of which is especially reactive. However, in these carefully designed inhibitors, the target enzyme recognizes them as substrates, causing eliminations and/or rearrangements such that there results an allyl-sulfoxide which then is in equilibrium with the corresponding allyl sulfenate which in turn deactivates the enzyme following attack of the sulfur by a nucleophile of the enzyme.

It is, therefore, an object of this invention to provide novel organic sulfoxides wherein one of the substituents on the sulfur carries such other functional group or groups as to be a latent allyl group which becomes unmasked upon reaction with a target enzyme and which function as suicide type inhibitors of transpeptidase and $\beta$-lactamase.

It is another object of this invention to provide a useful tool of biochemical research in the form of selective, very active inhibitors of transpeptidase and $\beta$-lactamse.

It is a further object of this invention to provide means for inhibiting those enzymes, both in vitro and in vivo with the novel organic sulfoxides of this invention.

It is a still further object to provide a method of treating bacterial infection, which comprises the administration of an effective amount of an enzyme inhibitor of this invention.

It is also an object of this invention to provide pharmaceutical formulations comprising one or more of the novel enzyme inhibitors of this invention.

DETAILED DESCRIPTION OF THE INVENTION

This invention comprises, as one embodiment, a new class of $K_{cat}$ or suicide enzyme inhibitors, which are organic sulfoxides of formula:

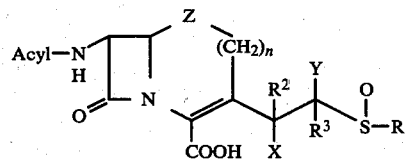

wherein Acyl is thienylacetyl, phenylacetyl, phenoxyacetyl or mandeloyl;

Z is S, S(o), N—($C_{1-3}$ alkyl), $CH_2$ or 0;

n is 0 or 1;

R is (a) phenyl, either unsubstituted or substituted with such as:
(1) nitro,
(2) cyano,
(3) $C_{1-3}$ alkylsulfonyl,
(4) $C_{1-3}$ alkoxycarbonyl,
(5) o-$C_{1-3}$ alkyl,
(6) o,o'-di($C_{1-3}$ alkyl), or
(7) di(trifluoromethyl);

(b) trihalomethyl such as
(1) trifluoromethyl, or
(2) trichloromethyl;

(c) 5–6 membered heteroaryl such as
(1) thiazolyl, (2) imidazolyl,
(3) pyridinyl,
(4) pyrazinyl,
(5) oxazolyl,
(6) pyrimidinyl, or
(7) thienyl; and Y is hydrogen; and X is chloro, fluoro, bromo, iodo, $C_{1-3}$ alkanoyloxy, toluenesulfonyl, benzenesulfonyloxy, $C_{1-3}$ alkanesulfonyloxy, trifluoroacetyloxy, p-nitrobenzoyloxy, p-nitrophenoxy, or the like;

X and Y taken together form a double bond;

$R^2$ is hydrogen, or an electron withdrawing group such as fluoro, chloro, $C_{1-3}$ alkoxycarbonyl, cyano, trifluoromethyl or the like; and $R^3$ is hydrogen or $C_{1-3}$ alkyl.

Pharmaceutically acceptable salts are also contemplated to be within the scope of the present invention and are the alkali metal salts, such as the sodium and potassium salts of the acidic enzyme inhibitors. These salts and others such as those resulting from synthetic procedures are readily interconvertible from one to another by well-known methods.

The novel enzyme inhibitors of this invention have a high, specific activity and thus are useful tools for the research biochemist and pharmacologist in studies of biochemical changes in vitro, and in vivo, and in biochemical assays for natural enzyme substrates and the like. The enzyme inhibitors are active, in vitro, at concentrations as low as about 0.1 mM but are generally employed at concentrations of 1 to about 2 mM.

For in vivo studies, the novel enzyme inhibitors of this invention are administered orally or parenterally, preferably the latter and preferably intravenously. Dosages of about 0.1 mg/kg to about 50 mg/kg are used depending on the purpose of the experiment, which may require the use of the threshold dose or the dose to produce total inhibition of a particular enzyme.

Generally the novel enzyme inhibitors of this invention produce the desired antibacterial effect when administered at from 0.1 to about 500 mg/kg body weight, preferably at from 1 to about 50 mg/kg of body weight. The preferred form of delivery of the instant compounds to domestic animals is by solution in drinking water or by inclusion in preformulated feedstuffs. For human and animal administration, any of the usual pharmaceutical oral forms may be employed such as tablets elixirs, aqueous suspensions or the like comprising from about 0.1 to about 500 mg of the compounds of this invention. Sterile solutions (representatively given for human treatment) for injection comprising from about 0.1 to about 500 mg of the compounds of this invention given two to four times daily are also suitable means of delivery.

The novel process for preparing the novel compounds of this invention comprises oxidation of an aromatic thio compound of structure:

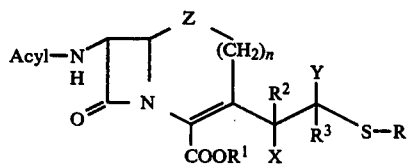

wherein Acyl, Z, n, $R^2$, $R^3$, R, X and Y are as previously defined and $R^1$ is a protective ester group. The nature of the ester group is not important except that it should be easily removable. It is preferred that $R^1$ be diphenylmethyl, p-methoxybenzyl, methoxymethyl, or p-nitrobenzyl.

The oxidizing agent is such as 1-chlorobenzotriazole $H_2O_2/V_2O_5$, $SO_2Cl_2/H_2O$/silica gel, $Cl_2$, $Br_2$, $NaIO_4$, acetyl nitrate, $Tl(NO_3)_3$, or a peracid such as m-chlorperbenzoic acid, preferably the latter. The oxidation with a peracid is conducted at temperatures from $-70°$ C. to about 30° C., preferably at about 0°-25° C., in an organic solvent such as an aromatic solvent, for example benzene, toluene or the like; or a chlorinated hydrocarbon such as tetrachloroethylene, chloroform, methylene chloride or the like, for times of a few minutes to about 4 hours.

After the oxidation is substantially complete, the protective group is removed by standard procedures such as treatment with a strong organic acid such as trifluoroacetic acid; a strong mineral acid such as hydrochloric acid; or a strong base such as sodium or potassium hydroxide. It is preferred to employ trifluoroacetic acid in anisole at $-10°$ C. to about $+10°$ C. for 1 to about 60 minutes, preferably 1 to about 5 minutes.

EXAMPLE 1

3-(1-Fluoro-2-[p-nitrophenylsulfinyl]ethyl)-4-carboxy-7-(2-thienyl)acetamidocephem Step A: Preparation of benzhydryl 3-(1-chloro-2-[p-nitrophenylthio]ethyl)-7-(2-thienyl)-acetamidocephem-4-carboxylate (I)

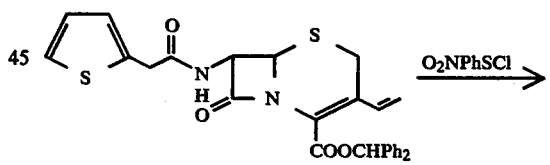

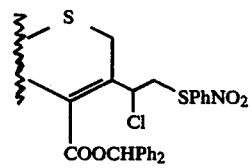

I

To a solution of 516 mg (1 mmole) of benzhydryl-3-vinyl-7-(2-thienyl)acetamidocephem-4-carboxylate in 25 ml of $CH_2Cl_2$ at $-18°$ C. is added over 30 minutes a solution of 190 mg (1 mmole) of p-nitrophenylsulfenyl chloride in 10 ml of $CH_2Cl_2$. The reaction is aged 30 minutes at 25° and evaporated to afford compound I.

Step B: Preparation of benzhydryl 3-(1-fluoro-2-[p-nitrophenylthio]ethyl)-7-(2-thienyl)acetamidocephem-4-carboxylate (II)

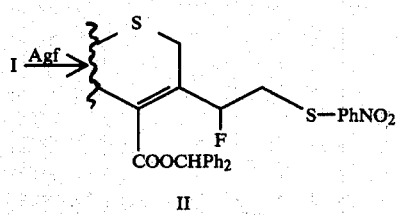

II

Compound I, 706 mg (1 mmole), is stirred overnight in dry acetonitrile with 127 mg (1 mmole) of AgF. The precipitated AgCl is separated by centrifugation and the solvent is evaporated, leaving compound II.

Step C: Preparation of benzhydryl 3-(1-fluoro-2-[p-nitrophenylsulfinyl]ethyl)-7-(2-thienyl)acetamidocephem-4-carbonylate (III)

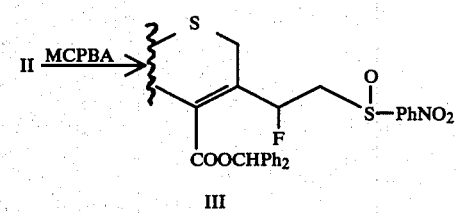

III

To 689 mg (1 mmole) of compound II, in 25 ml of $CH_2Cl_2$ at 0° C. is added dropwise over 1 hour a solution of 203 mg of MCPBA (85%; 1 mmole) in 20 ml of $CH_2Cl_2$. The reaction is aged 30 minutes at 25° C. and washed successively with aqueous $NaHCO_3$ and brine. Evaporation of the solvent provides compound III.

Step D: Preparation of 3-(1-fluoro-2-[p-nitrophenylsulfinyl]ethyl)-4-carboxy-7-(2-thienyl)acetamidocephem (IV)

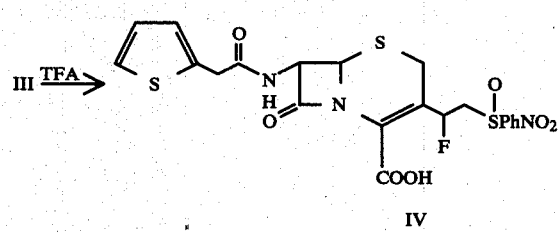

IV

Compound III, 705 mg (1 mmole), is taken up in 5 ml of anisole and cooled to 0° C. TFA, 25 ml, is added at 0° C. and the reaction aged 2 minutes at 0° C. The TFA and anisole are then pumped off at 30° C., 0.1 Torr, and the residue is partitioned between $CHCl_3$ and aqueous $NaHCO_3$. The aqueous portion is acidified to pH 2 with $H_3PO_4$ at 0° C. and extracted 3x with ethyl acetate. The organic extracts are combined, washed with brine, dried with $MgSO_4$, filtered and evaporated to afford compound IV.

Employing the procedure substantially as described in Example 1, Steps A through D, but substituting for the p-nitrophenylsulfenyl chloride used in Step A an equimolecular amount of a compound of formula R-SCl, wherein R is as previously defined, there are produced the corresponding 3-(1-fluoro-2-[R-sulfinyl]ethyl-4-carboxy-7-(2-thienyl)acetamidocephems.

EXAMPLE 2

7β-(2-Thienyl)acetamido-3-(p-nitrophenylsulfinylmethylene)decephalosporanic acid

Step A: Preparation of dimethyl-p-nitrobenzylphosphonate

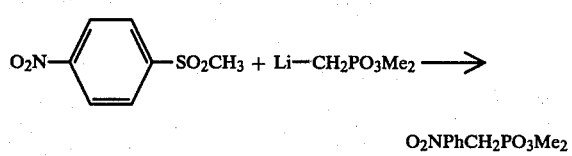

$O_2NPhCH_2PO_3Me_2$

To 0.257 g $CH_3PO_3Me_2$ (2.07 mmoles) in 3 ml THF, at −78°, under $N_2$, is added 1.34 ml of 1.7 M BuLi (2.28 mmoles). The mixture is stirred 30 minutes at −78°, and then treated with 0.201 g (1 mmol) of $O_2NPhSO_2Me$ in 2 ml THF. It becomes dark. After 15 minutes at −78°, it is warmed over 10 minutes to −10°, and then treated with 10 ml water+3 ml of 1 M aqueous pH 2 $H_3PO_4$. The mixture is extracted 3× with $CH_2Cl_2$. The organic layers are combined and washed with aqueous $K_2HPO_2$, dried with $MgSO_4$, filtered and evaporated, to a residue of 0.234 g. The product is purified by PLC on silica gel, 20×20 cm, 2 mm layer, EtOAc, Rf about 0.2, affording 122 mg (0.416 mmoles) pure product, m.p. 132°, 42%.

Step B: Preparation of 7β-(2-thienyl)acetamido-3-(p-nitrophenylsulfinylmethylene)decephalosporanic acid

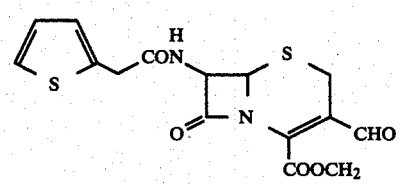

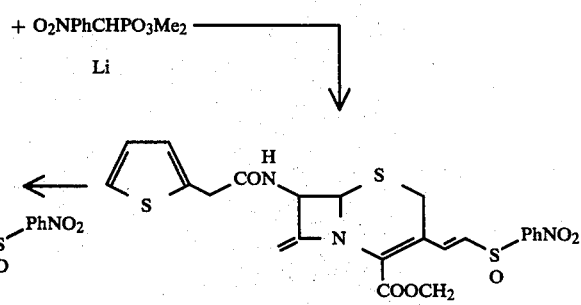

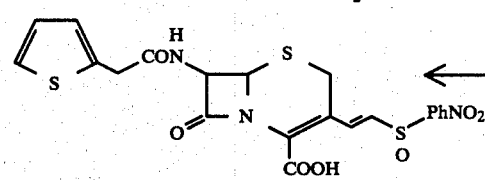

To 518 mg (1 mmol) benzyhydryl 7β-(2-thienyl)acetamido-3-oxo-decephalosporanate in 10 ml THF at −78°, under $N_2$, is added successively 1 mmol BuLi and 127 mg TMS-Cl. Separately, 293 mg (1 mmol) dimethyl-p-nitrobenzylphosphonate in 5 ml THF, −78°, under $N_2$, is treated with 1 mmol BuLi. The two solutions are combined, kept 1 hour at −78° and then warmed to room temperature over 30 minutes. The reaction mixture is treated with 50 ml water +pH 2 $H_3PO_4$ and extracted with EtOAc. The organic layer is washed with $H_2O$, aqueous $K_2HPO_4$, dried with $MgSO_4$, filtered, evaporated, taken up in 1 ml of anisole, treated with 5 ml of TFA 2 minutes at 0°, and evaporated at 0.5 mm, and 30°. The residue is taken into water, washed with $CH_2Cl_2$, the pH made to 2.5, and extracted with EtOAc. The EtOAc is washed with brine and evaporated to afford the final product.

EXAMPLE 3

Tablets containing 1.0, 2.0, 25.0, 50.0 and 100.0 mg, respectively of 1-amino-2-chloro-3-p-nitrophenylsulfinyl propane (active compound) are prepared as illustrated below:

|  | Amount - mg/tablet | | | | |
|---|---|---|---|---|---|
| Active Compound | 1.0 | 2.0 | 25.0 | 50.0 | 100.0 |
| Microcrystalline cellulose | 49.25 | 48.75 | 37.25 | 100.0 | 200.0 |
| Modified food corn starch | 49.25 | 48.75 | 37.25 | 4.25 | 8.5 |
| Magnesium stearate | 0.50 | 0.50 | 0.50 | 0.75 | 1.5 |

All of the active compound cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 50.0 mg, and 100.0 mg of active compound per tablet.

Other tablets are prepared using the same procedures and the equivalent amounts of excipients along with equivalent amounts of the other active compounds of the present invention.

EXAMPLE 4

| Injectable Preparation | |
|---|---|
| 3-(1-fluoro-2-[p-nitrophenylsulfinyl]ethyl)-4-carboxy-7-(2-thienyl)acetamidocephem | 25 mg |
| Pyrogen fee water to | 1 ml |

Sterilize by filtration and seal under nitrogen.
What is claimed is:
1. A compound of structural formula

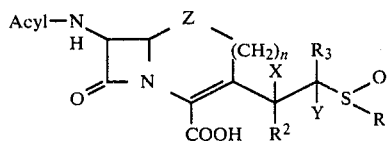

or a pharmaceutically acceptable salt thereof wherein:
Acyl is thienylacetyl, phenylacetyl, phenoxyacetyl or mandeloyl;
Z is S, or S(o);
R is
(a) phenyl or phenyl substituted with:
  (1) nitro,
  (2) cyano,
  (3) $C_{1-3}$alkylsulfonyl,
  (4) $C_{1-3}$alkoxycarbonyl,
  (5) o-$C_{1-3}$alkyl,
  (6) o,o'-di($C_{1-3}$alkyl), or
  (7) di(trifluoromethyl);
(b) trihalomethyl;
(c) 5-6 membered heteroaryl selected from:
  (1) thiazolyl,
  (2) imidazolyl,
  (3) pyridinyl,
  (4) pyrazinyl,
  (5) oxazolyl,
  (6) pyrimidinyl, and
  (7) thienyl; and n=1;
Y is hydrogen;
X is chloro, fluoro, bromo, iodo, $C_{1-3}$alkanoyloxy, toluenesulfonyloxy, benzenesulfonyloxy, $C_{1-3}$alkanesulfonyloxy, trifluoroacetoxy, p-nitrobenzoyloxy, or p-nitrophenoxy; or
X and Y taken together form a double bond;
$R^2$ is hydrogen, fluoro, chloro, $C_{1-3}$alkoxycarbonyl, cyano or trifluormethyl; and
$R^3$ is hydrogen or $C_{1-3}$alkyl.

2. A pharmaceutical antibacterial composition comprising a pharmaceutical carrier and an effective antibacterial amount of a compound of structural formula:

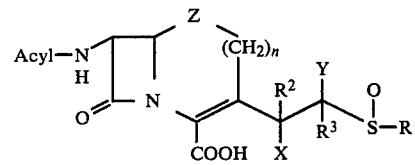

or a pharmaceutically acceptable salt thereof wherein:
Acyl is thienylacetyl, phenylacetyl, phenoxyacetyl or mandeloyl;
Z is S, or S(o);
R is
(a) phenyl or phenyl substituted with:
  (1) nitro,
  (2) cyano,
  (3) $C_{1-3}$alkylsulfonyl,
  (4) $C_{1-3}$alkoxycarbonyl,
  (5) o-$C_{1-3}$alkyl,
  (6) o,o'-di($C_{1-3}$alkyl), or
  (7) di(trifluoromethyl);
(b) trihalomethyl;
(c) 5-6 membered heteroaryl selected from:
  (1) thiazolyl,
  (2) imidazolyl,
  (3) pyridinyl,
  (4) pyrazinyl,
  (5) oxazolyl,
  (6) pyrimidinyl, and
  (7) thienyl; and n=1;
Y is hydrogen;
X is chloro, fluoro, bromo, iodo, $C_{1-3}$alkanoyloxytoluenesulfonyoxy, benzenesulfonyloxy, $C_{1-3}$alkanesulfonyloxy, trifluoroacetoxy, p-nitrobenzoyloxy, or p-nitrophenoxy; or X and Y together form a double bond;

$R^2$ is hydrogen, fluoro, chloro, $C_{1-3}$alkoxycarbonyl, cyano or trifluoromethyl; and $R^3$ is hydrogen or $C_{1-3}$alkyl.

3. A method of treating a bacterial infection in a patient in need of such treatment which comprises the administration of an effective antibacterial amount of a compound of structural formula:

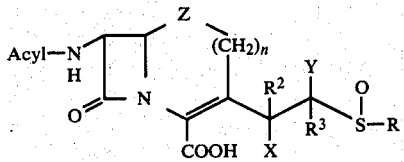

or a pharmaceutically acceptable salt thereof wherein:

Acyl is thienylacetyl, phenylacetyl, phenoxyacetyl or mandeloyl;

Z is S, or S(o);

R is (a) phenyl or phenyl substituted with:
 (1) nitro,
 (2) cyano,
 (3) $C_{1-3}$alkylsulfonyl,
 (4) $C_{1-3}$alkoxycarbonyl,
 (5) o-$C_{1-3}$alkyl,
 (6) o,o'-di($C_{1-3}$alkyl), or
 (7) di(trifluoromethyl);

(b) trihalomethyl;

(c) 5–6 membered heteroaryl selected from
 (1) thiazolyl,
 (2) imidazolyl,
 (3) pyridinyl,
 (4) pyrazinyl,
 (5) oxazolyl,
 (6) pyrimidinyl, and
 (7) thienyl; and n=1;

Y is hydrogen;

X is chloro, fluoro, bromo, iodo, $C_{1-3}$alkanoyloxy, toluenesulfonyloxy, benzenesulfonyloxy, $C_{1-3}$alkanesulfonyloxy, trifluoroacetoxy, p-nitrobenzoyloxy or p-nitrophenoxy; or X and Y together forms a double bond;

$R^2$ is hydrogen, fluoro, chloro, $C_{1-3}$alkoxycarbonyl, cyano, or trifluoromethyl; and $R^3$ is hydrogen or $C_{1-3}$alkyl.

4. The compound of claim 1 which is:
3-(1-fluoro-2-[p-nitrophenylsulfinyl]ethyl)-4-carboxy-7-(2-thienyl)acetamidocephem, or
3-(2-[p-nitrophenylsulfinyl]ethenyl)-4-carboxy-7-(2-thienyl)acetamidocephem.

5. The pharmaceutical composition of claim 2 wherein the compound is:
3-(1-fluoro-2-[p-nitrophenylsulfinyl]ethyl)-4-carboxy-7-(2-thienyl)acetamidocephem, or
3-(2-[p -nitrophenylsulfinyl]ethenyl)-4-carboxy-7-(2-thienyl)acetamidocephem.

6. The method of claim 3 wherein the compound is:
3-(1-fluoro-2-[p-nitrophenylsulfinyl]ethyl)-4-carboxy-7-(2-thienyl)acetamidocephem, or
3-(2-[p-nitrophenylsulfinyl]ethenyl)-4-carboxy-7-(2-thienyl)acetamidocephem.

* * * * *